United States Patent [19]
Hughes

[11] Patent Number: 5,919,217
[45] Date of Patent: Jul. 6, 1999

[54] PORTABLE PHOTOTHERAPY UNIT

[75] Inventor: Philip C. Hughes, Lake Hopatcong, N.J.

[73] Assignee: Medic-Light, Inc., Lake Hopatcong, N.J.

[21] Appl. No.: 08/048,173

[22] Filed: Apr. 15, 1993

Related U.S. Application Data

[63] Continuation of application No. 07/918,937, Jul. 22, 1992, abandoned, which is a continuation of application No. 07/754,177, Aug. 27, 1991, abandoned, which is a continuation of application No. 07/574,382, Aug. 27, 1990, abandoned, which is a continuation of application No. 07/412,598, Aug. 17, 1989, abandoned, which is a continuation of application No. 07/129,985, Dec. 8, 1987, abandoned.

[51] Int. Cl.$^6$ ................................................ A61N 5/00
[52] U.S. Cl. ........................................ 607/90; 607/88
[58] Field of Search ........................... 607/80, 81, 88, 607/90, 91, 95; 362/103–106; 353/81; 351/203

[56] References Cited

U.S. PATENT DOCUMENTS

| | | | |
|---|---|---|---|
| 3,621,838 | 11/1971 | Harding et al. | 128/380 |
| 4,057,054 | 11/1977 | Giannone | 351/203 |
| 4,185,901 | 1/1980 | Behr | 353/81 |
| 4,287,554 | 9/1981 | Wolff | 128/396 |
| 4,553,534 | 11/1985 | Stiegler | 128/24.1 |
| 4,858,609 | 8/1989 | Cole | 128/395 |
| 5,292,345 | 3/1994 | Gerardo | 607/88 |

FOREIGN PATENT DOCUMENTS 338679  10/1903  France ................................ 128/396

OTHER PUBLICATIONS

Czeisler et al,; Bright Light Resets the Human Circadian Pacemaker Independent of the Timing of the Sleep–Wake Cycle *Science* 233:667–671; (1986).
Lewy et al. "Light Suppresses Melatonin Secretion in Humans" *Science* 210:1267–1269; (1980).
Neer "Environmental Light: Effects on Vitamin D Synthesis and Calcium Metabolism in Humans" *Annals of the NY Academy of Sciences* 453:14–20 (1985).
Rosenthal et al. "Seasonal Affective Disorder" Archives of General Psychiatry 41:72–80; (1984).
Wirz–Justice et al. "Light Treatment of Seasonal Affective Disorder in Switzerland" *Acta Psychiatrica Scandinavia* 74:193–204 (1986).
Phillips "Let the Sun Shine" *Chicago Tribune* Dec. 11, 1985.

*Primary Examiner*—Mark S. Graham
*Attorney, Agent, or Firm*—Darby & Darby

[57] ABSTRACT

A bright-light portable phototherapy unit to modify biological rhythms has a housing in which there is a source for producing light energy having a major portion in the visible light range. The housing is to be placed adjacent to the body of a user for positioning and directing the light from the source through an opening in the housing to be applied to the eyes of the user. The light source can be one or more fluorescent lamps and the light incident on the eyes preferably is at least 2,000 lux and, more preferably, at least 8,000 lux.

13 Claims, 2 Drawing Sheets

FIG. 1
FIG. 2
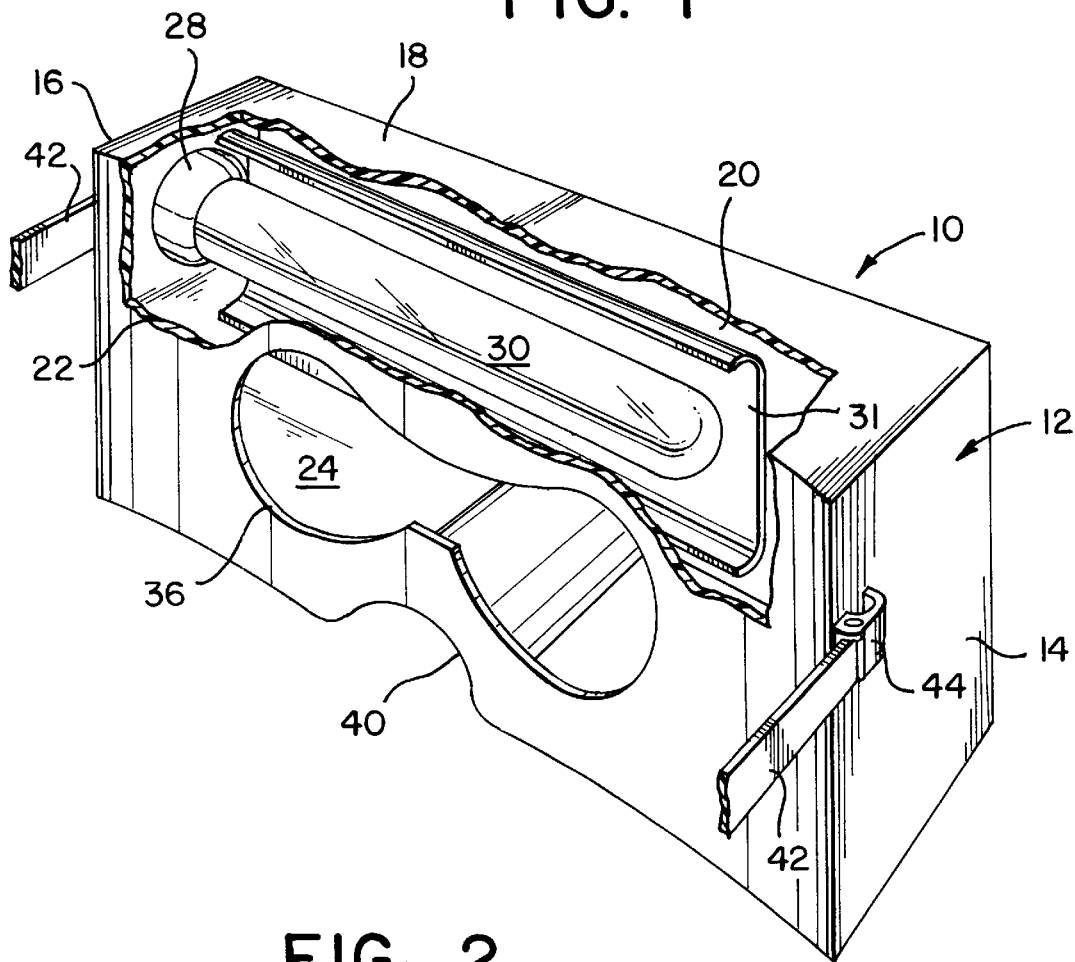
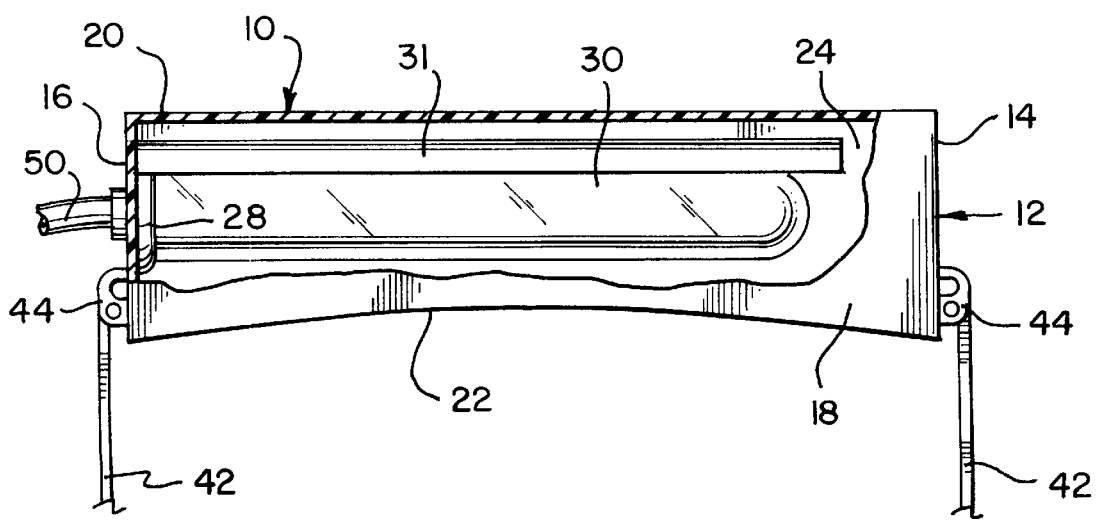

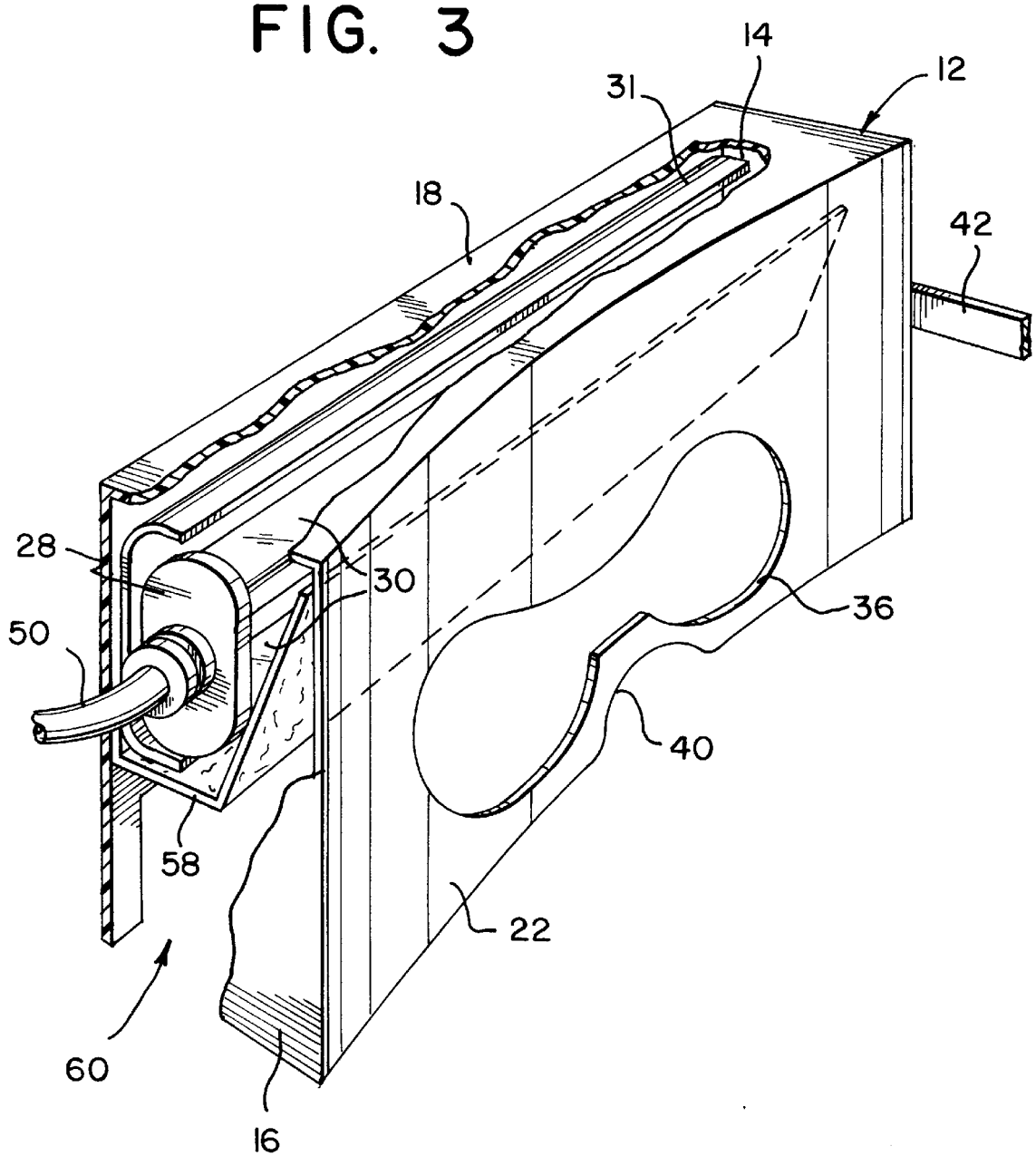

PORTABLE PHOTOTHERAPY UNIT

This is a continuation of application Ser. No. 07/918,937 filed Jul. 22, 1992, abandoned, which was a continuation of application Ser. No. 754.177, filed Aug. 27. 1991, abandoned, which was a continuation of application Ser. No. 574,382, filed Aug. 27, 1990, abandoned, which was a continuation of Ser. No. 412,598 filed Aug. 17, 1989, abandoned, which is a continuation of Ser. No. 129,985 filed Dec. 8, 1987, abandoned.

BACKGROUND OF THE INVENTION

Medical research has demonstrated that light can be used to treat a variety of disorders. Typical references showing the use of light to treat such disorders are in the following publications, which are illustrative of a number of such publications:

Czeisler, C. A., Allan J. S., Strogatz, S. H., Ronda, J. M., Sanchez, R., Rios, D., Freitag, W., O., Richardson, G. S., & Kronauer, R. E. (1986). Bright lights resets the human circadian pacemaker independent of the timing of the sleep-wake cycle. *Science* 233:667–671.

Lewy, A. J., Wehr, T. A., Goodwin, F. K., Newsome, D. A., & Markey, S. P. (1980) Light suppresses melatonin secretion in humans. *Science* 210:1267–1269.

Neer, R. M. (1985) Environmental light: effects of Vitamin D synthesis and calcium metabolism in humans. *Annals of the New York Academy of Sciences* 453:14–20.

Rosenthal, N. E., Sack, D. A., Gillin, J. D., Lewy, A. J., et al. (1984) Seasonal affective disorder: A description of the syndrome and preliminary findings with light therapy. *Archives of General Psychiatry* 41:72–80.

Terman, M., Terman, J. S., Quitkin, F. M., McGrath, P. J., & Stewart, J. W. (1987) Light therapy for Seasonal Affective Disorder: A review of efficacy.

Wirz-Justice, A., Bucheli, C., Graw, P., Kielholz, P., et al (1986) Light treatment of seasonal effective disorder in Switzerland. *Acta Psychiatrica Scandinavica* 74:193–204.

In summary, the above publications and others show that light has been and can be used to treat seasonal affective disorder (SAD), adjust the circadian rhythm, enhance mood, decrease fatigue, treat jet lag, etc.

In the past, the light has been administered by using banks of fluorescent lamps grouped together to produce light intensities in the range of from about 2,000 to about 10,000 lux. Units for producing high intensity light in the range of from about 7,000 to 10,000 lux or more have been demonstrated to be effective in carrying out the necessary phototherapy treatment over much shorter time periods than where the light intensity is in the lower range say about 2,000–3,000 lux. In either prior method of treatment, the light units were of the type using fluorescent lamp tubes of standard length, e.g., 24" through 92", and the user sits two-three feet from the unit to receive the necessary light intensity. Consequently, his movement is restricted.

BRIEF DESCRIPTION OF THE PRESENT INVENTION

The present invention is directed to a phototherapy unit of substantially reduced size and, which also can be made portable. This unit includes one or more compact fluorescent lamp(s), i.e., fluorescent lamps of a small size such as in the range 0"–9" mounted in a manner such that they can be fully portable or permit the user to have range of movement without having any reduction in light intensity. In addition, a preferred embodiment of the unit permits the user to have the benefits of the high intensity light while performing a normal task such as reading or office work.

This is accomplished in a preferred embodiment of the present invention by mounting one or more compact fluorescent lamps in a housing which can be positioned to correspond to the user's eye position and, because of the close proximity of the eyes to the light source, the user receives a high light intensity from a small light source. The light source itself is small and consumes relatively little power. The use of a compact fluorescent provides a linear light source rather than point source, thus allowing for even diffusion of light across field of view and uniform brightness when used with the proper reflective material and diffuser.

The housing can be of a type to be held directly on the user's head or held by an adjustable type stand. Further, in the preferred embodiment the housing has a light reflector and diffuser lens or prism which maintains the light in a superior position to the eyes, i.e., above the horizontal line of sight, which permits the user to view an object such as written material while still receiving the light.

Object of the Invention

It is therefore an object of the present invention to provide a phototherapy unit of a reduced size.

An additional object is to provide a phototherapy unit using one or more compact type fluorescent lamps.

A further object is to provide a phototherapy unit using a linear light source rather than point source.

Another object is to provide a high intensity phototherapy unit which can be made portable or semi-portable to permit the user to continue performing normal tasks.

Yet another object is to provide a compact phototherapy unit which is mounted close to the eyes of the user and can be either carried by the user or carried on an adjustable stand.

BRIEF DESCRIPTION OF THE DRAWING

Other objects and advantages of the present invention will become more apparent upon reference to the following specification annexed drawings in which:

FIG. 1 is a front perspective view of one form of the unit and its housing;

FIG. 2 is a top view of the embodiment of FIG. 1; and

FIG. 3 is a view of a portion of another unit which can be used for reading or working at the same time that the user receives the light.

BRIEF DESCRIPTION OF THE INVENTION

Referring to FIGS. 1 and 2, the phototherapy unit 10 of the present invention includes a housing 12 whose parts are preferably molded of plastic or other suitable material having sidewalls 14 and 16, a top wall 18, front wall 20, back wall 22 and bottom wall 24. The back wall 22, that is, the wall to be closer to the eyes of the user, is preferably curved to generally conform to the shape of the face of a human user. The distance between the two end walls 14 and 16 is the size of the width of a human head.

Back wall 22 has a cut out 36 of a shape to accomodate the eyes of a human user who is to look into the interior of the housing. A bridge 40 is formed in the bottom wall 24 front and back walls 20, 22 so that the complete housing unit 12 can rest on the nose of the user. An ear piece arm 42 is mounted by a hinge 44 to each side wall 14 and 16. Each arm has an end (not shown) which fits around an ear of the user. Alternatively, a strap can be provided. Thus, the entire housing 12 can be held on the bridge of the nose and by the arms 42 or a strap so that the user can look directly into the housing interior.

Mounted to one of the side walls 16 is a socket 28 to accept, hold and make electrical contact with the terminals of a respective compact twin-tubed fluorescent lamp 30. Such a lamp is well known in the trade. A single tube incandescent lamp also can be used. The lamp is to be positioned slightly above the eyes as shown in FIG. 1 30.

An elongated, curved reflector 31 has its end attached to a respective end wall 16 and is in back of the lamp to reflect its light down toward the eye opening 36. Reflector 31 is attached to a respective side wall by a suitable fastening arrangement, for example, forming a groove in the side wall and fastening the reflector therein by a suitable adhesive.

A lead wire 50 extends from the lamp receptacle 28 through the corresponding side wall 16. These wires are connected to a suitable power supply for the lamp 30. The power supply can be either of the rechargeable battery type (not shown) or else directly to an alternating current main's supply, with the appropriate ballast transformer being supplied for operational requirements and safety purposes.

That is, if the lamps are to be operated via an A.C. supply, the user will be restricted to movement in accordance with the length of the lead wire wire 50. If the lamp is to be operated by batteries, then the user can carry the batteries so that the phototherapy unit is fully portable.

The lamp 30 perferably is of the full spectrum color temperature, i.e., 5000–5500 k type. That is, it produces a spectrum having a high color rendering index and corresponding color temperature. A full spectrum standard size fluorescent lamp of this type is sold by Duro-Test Corporation under the trademark VITA-LITE. The phosphor blend of that lamp is preferably used with the compact lamp 30. It is believed that the full spectrum light output produces the most beneficial photobiological effect. However, only the visible energy of the full spectrum light is or may be necessary, with the light intensity of major interest. Thus, other compact fluorescents or tubular incandescents may be used in unit.

Even small, tubular incandescent lamps also can be used. Here also, the lamps must have the required lumen output and preferably a high color rendering index. In general, the incandescent lamp has low efficacy, i.e., lumens/watt, compared to the fluorescent lamp, with much of its energy emitted in the infrared spectrum as heat. Special filters and/or coatings could be used to meet the required lumen output.

A piece of light diffusing material for example plastic,or lens or prism 568, is located between the lamp 30 and the eye opening 36. This spreads the light out more evenly and keeps it above the line of sight, allowing for downward gaze and vision.

The overall size of the phototherapy unit housing 12 is about 7" by 4½" by 3" and it can be worn on the head like goggles.

A suitable fluorescent lamp of the compact, twin tube type (F9TT/41) has about 9 watts output, is about 6.5" in length including base and has sufficient initial lumen output to provide about 10,000 lux when placed close to the eyes. Thus, the user can receive a photobiological light dosage of up to about 10,000 lux. A smaller lamp tube version of lesser watts current consumption can be used to produce less than 5000 lux and can be used effectively with longer exposure times. Even lower levels can be produced using filters. Where two lamps are used, each can have a different energy output spectrum.

As indicated, phototherapy has generally been carried out with light levels in the range of 2,500–10,000 lux by the patient sitting in front of large size light boxes, i.e., 2' by 2' to 2' by 4' or larger. As is well known, the intensity of illumination varies inversely as the square of the distance. Whereas the patient would have to sit from within two-three feet of the light box to receive their required dosage, with the phototherapy unit of the present invention, the light source is very close and, consequently, the intensity level provided by small lamps is adequate.

While it is preferred that a full-spectrum or daylight type color temperature light source be utilized, it should be understood that other types of light sources of the compact type also can be used. It is preferred that the light source have at least a high color rendering index, e.g., above so as measured by the CIE scale and preferably above 80–90.

FIG. 3 shows a modification of the invention. Here a lens, prism or optical diffuser 58 is mounted in front and superior of the eye opening 36. In addition, there is no bottom wall 24 and no lower back wall 22 for the housing but open space 60 so that user can look down at an object such as material on a desk.

The prism, lens 58 is configured such that the light from the fluorescent lamp or lamps is transmitted through the prism, lens from a superior forward position toward the eye opening 36 so that the user receives the required light intensity. However, by looking below or inferior to the horizontal line of sight, the user can see out of the housing bottom or lower front section, so that, for example, he can be reading at the same time he is receiving the light from above through the eye opening.

In a variation of the phototherapy unit 10, instead of having the housing 12 constructed to be mounted on the face of the user by means of the arm 42 or strap, it is attached by an adjustable holder, like the frame for fluorescent desk lamp which is separately mounted to a base member, chair, desk, etc. By using this arrangement, the housing 12 is totally self-supporting and can be brought close to the face or the eye of the user and adjusted. It is preferred that a universal type of holder be utilized which provides all of the degrees of freedom necessary.

The phototherapy unit of the present invention is highly useful since it provides a high degree of freedom of use for a patient who can be receiving phototherapy treatment while at the same time not have to be confined to a particular location such that he cannot move around. Also, it reduces the size of the unit which make treatment easier to administer so that more people will accept and use the treatment. It can also be used in airplanes by plugging into an overhead, power outlet so that one can prepare for arrival in different time zones, especially overseas flights, to avoid symptoms of jet lag. The unit is turned on to correspond to sunrise at the destination point when going East and before sunset when traveling West.

What is claimed is:

1. A bright-light phototherapy unit to modify biological rhythms comprising:

a source for producing light energy the major portion of which is in the visible light range, means to be placed adjacent to the body of a user for substantially fixedly positioning and directing the light from said source to be applied directly within a few inches of the eyes of the user so that the major portion of the visible light from the source will be provided to the eyes of the user irrespective of the orientation of the head of the users, wherein said positioning and directing means comprises a housing, said light source being located within said housing, said housing having an opening therein into which the user looks for permitting the user's eyes to receive the light from the source, and wherein said source comprises an elongated linear fluorescent lamp within said housing, said housing having an elongated opening in proximity to both eyes for light to be provided across the width of both eyes of the user.

2. A phototherapy unit as in claim 1 where the light output of said unit received by the user's eyes is at least 2,000 lux.

3. A phototherapy unit as in claim 1 where the light output of said unit received by the user's eyes is at least 8,000 lux.

4. A bright-light phototherapy unit to modify biological rhythms comprising:

a source for producing light energy the major portion of which is in the visible light range, means to be placed adjacent to the body of a user for substantially fixedly positioning and directing the light from said source to be applied directly within a few inches of the eyes of the user so that the major portion of the visible light from the source will be provided to the eyes of the user irrespective of the orientation of the head of the user, wherein said positioning and directing means comprises a housing, said light source being located within said housing, said housing having an opening therein, into which the user looks for permitting the user's eyes to receive the light from the source, and wherein said light source comprises one or more small fluorescent lamps.

5. A bright-light phototherapy unit to modify biological rhythms comprising:

a source for producing light energy the major portion of which is in the visible light range, means to be placed adjacent to the body of a user for substantially fixedly positioning and directing the light from said source to be applied directly within a few inches of the eyes of the user so that the major portion of the visible light from the source will be provided to the eyes of the user irrespective of the orientation of the head of the user, wherein said positioning and directing means comprises a housing, said light source being located within said housing, said housing having an opening therein into which the user looks for permitting the user's eyes to receive the light from the source, further comprising means for holding said housing adjacent the face of the user, wherein said holding means comprises an adjustable fixture for holding said housing, and wherein said housing has an opening at the bottom thereof, said viewing means comprises an optical means to make the user's field of view out of the bottom and/or lower front portion of the housing.

6. A phototherapy unit as in claim 5 wherein the light output of said unit to the eyes of the user is at least 2,000 lux.

7. A bright-light uhototherapy unit to modify biological rhythms comprising:

a source for producing light energy the major portion of which is in the visible light range, means to be placed adjacent to the body of a user for substantially fixedly positioning and directing the light from said source to be applied directly within a few inches of the eyes of the user so that the major portion of the visible light from the source will be provided to the eyes of the user irrespective of the orientation of the head of the user wherein said light source produces a full spectrum light having visible and ultraviolet energy in the light output spectrum.

8. A bright-light phototherapy unit to modify biological rhythms comprising:

a source for producing light energy the major portion of which is in the visible light range, and means to be placed adjacent to the body of a user for substantially fixedly Positioning and directing the light from said source to be applied directly within a few inches of the eyes of the user so that the major portion of the visible light from the source will be provided to the eyes of the user irrespective of the orientation of the head of the user, and wherein the light output of said unit to the eyes of the user is at least 5,000 lux.

9. A bright-light phototherapy unit to modify biological rhythms comprising:

a source for producing light energy the manor portion of which is in the visible light range, and means to be placed adjacent to the body of a user for substantially fixedly positioning and directing the light from said source to be applied directly within a few inches of the eyes of the user so that the major portion of the visible light from the source will be provided to the eyes of the user irrespective of the orientation of the head of the user, and wherein the light output of said unit to the eyes of the user is at least 8,000 lux.

10. A phototherapy unit to modify biological rhythms comprising:

a source for producing light energy the major portion of which is in the visible light range;

a housing to which said source is mounted to be carried on the body of the person being treated for holding the positional relationship of the light originating from the source substantially fixed irrespective of the motion of the head of the person being treated with the light being applied directly into the eyes of the person being treated from a location at a substantially fixed distance within a few inches of the person's eyes, and wherein said source comprises an elongated lamp to provide the light to both of the eyes of the person being treated.

11. A phototherapy unit as in claim 10 wherein said source comprises an elongated linear fluorescent lamp and wherein said housing has an elongated opening for light to be provided across the width of both eyes of the user.

12. A phototherapy unit as in claim 11 wherein the light output of said unit received by the user's eyes is at least 8,000 lux.

13. A phototherapy unit as in claim 10 were the light output of said unit received by the user's eyes is at least 2,000 lux.

* * * * *